United States Patent [19]

Andresen et al.

[11] 4,181,135

[45] Jan. 1, 1980

[54] METHOD AND APPARATUS FOR MONITORING ELECTROCARDIOGRAPHIC WAVEFORMS

[75] Inventors: Richard P. Andresen, Belmont; Robert M. Armington, Boston; Robert L. Cannon, III, Waltham; Andrew J. Griffin, Framingham, all of Mass.

[73] Assignee: American Optical Corporation, Southbridge, Mass.

[21] Appl. No.: 883,096

[22] Filed: Mar. 3, 1978

[51] Int. Cl.² ............................................. A61N 5/04
[52] U.S. Cl. .................................................... 128/703
[58] Field of Search ...................... 128/2.06 A, 2.06 R

[56] References Cited

U.S. PATENT DOCUMENTS

| | | | |
|---|---|---|---|
| 3,267,934 | 8/1966 | Thornton | 128/2.06 A |
| 3,352,300 | 11/1967 | Rose | 128/2.06 A |
| 3,518,983 | 7/1970 | Jorgensen | 128/2.06 A |
| 3,524,442 | 8/1970 | Horth | 128/2.06 A |
| 3,616,790 | 11/1971 | Harris | 128/2.06 A |
| 3,654,916 | 4/1972 | Neilson | 128/2.06 A |
| 3,658,055 | 4/1972 | Abe et al. | 128/2.06 A |
| 3,699,946 | 10/1972 | Michel | 128/2.06 A |
| 3,903,874 | 9/1975 | Shakespeare | 128/2.06 A |
| 3,939,824 | 2/1976 | Arneson et al. | 128/2.06 A |
| 3,998,214 | 12/1976 | Garrison | 128/2.06 A |

Primary Examiner—William E. Kamm
Attorney, Agent, or Firm—Jeremiah J. Duggan; Alan H. Spencer; Stephen A. Schneeberger

[57] ABSTRACT

Apparatus for the recognition of ventricular premature beats by an identifying width of a QRS complex by dividing the area by the height and further noting when the width measurements is at least 40% wider than the average width of the immediately preceding several QRS complexes. Additional apparatus for indicating ventricular premature beats by determination of an early width determination which exceeds the average width by at least 20% and is additionally followed by the compensatory pause as determined by interbeat interval measurement.

12 Claims, 7 Drawing Figures

METHOD AND APPARATUS FOR MONITORING ELECTROCARDIOGRAPHIC WAVEFORMS

BACKGROUND OF THE INVENTION

The invention relates to electrocardiographic monitoring systems, and more particularly to such systems which detect abnormal ECG waveforms.

In the field of cardiology, as practiced both within the hospital and upon ambulatory patients, it is common to continuously monitor the ECG signal of a patient for analysis. Normally it is impractical for a doctor or other trained personnel to continuously monitor the ECG waveform and, accordingly, systems have evolved for automatically monitoring and analyzing the waveform. In some instances, this monitoring equipment may operate on a real-time basis while ECG signals are being obtained from the patient. In yet other applications, particularly the field known as ambulatory or Holter-type monitoring, the patient's ECG signal may be recorded over a long interval and subsequently replayed, usually at an increased speed, for the requisite analysis.

The ECG waveform is normally comprised of a series of characteristic points conventionally designated by the letters P, Q, R, S and T. The Q, R and S portions of the wave when taken together and referred to as the QRS complex. In most heart-monitoring systems, there is provided means for determining, in accordance with a preconceived method of formula, that the QRS complex has occurred. Such means are commonly referred to as R-wave detectors, a representative example of which being disclosed in U.S. Pat. No. 3,490,811 issued July 6, 1971, to Harris for Electrocardiographic R-Wave Detector. However, it is often desirable to further differentiate between a QRS complex which corresponds to a normal heart action, and a QRS complex which corresponds to abnormal heart action.

One such abnormal heart action to which particular attention has been directed is that of ectopic beats. Such ectopic beats are characterized by departure from a "normal" interbeat interval and/or departure from a "normal" waveform morphology. It will be appreciated that a "normal" interbeat interval and/or waveform morphology for one patient may differ from that which is "normal" for another. Certain ectopic beats deserving of special attention include ventricular premature beats (VPB), atrial premature beats (APB), and successive groupings of such premature beats.

Therefore, it is important to be able to analyze the ECG wave in a manner capable of rapidly and accurately identifying particular types of ectopic beats and characterizing them as such. It is further important that the analysis be applicable to the playback of prerecorded ECG waveforms as well as those received on a real-time basis.

Typically, ventricular premature beats (VPB's) have been identified by monitoring the interval between successive QRS complexes and the width and/or area of such complexes, and signaling the occurrence of such PVB if those parameters differ by more than a predetermined amount from that which is "normal" for the particular patient. An example of these techniques is disclosed in some detail in U.S. Pat. 3,616,791 issued Nov. 2, 1971, to G. J. Harris for Electrocardiographic Morphology Recognition System. In that patent, certain QRS complexes are identified as VPB's if their width is greater than normal. That determination of width is made by measuring the area under the rectified ECG signal and comparing it with the average area. That area determination is made by integrating the rectified waveform. Before actually indicating that a "wide" QRS complex is actually a VPB, the interval between QRS complexes is normally required to exhibit a so-called compensatory pause. The QRS complex of a VPB will usually occur earlier than expected and the next succeeding QRS complex will occur after a longer than normal interval or compensatory pause. This combination of a "wide" QRS complex occurring earlier than usual and followed by a compensatory pause is generally a reliable indicator of a VPB.

It would, however, be even more preferable to identify a VPB based on width alone without additionally requiring the analysis of the interbeat interval. However, such analysis has not heretofore been relied on, in part because the area, and thus the width measure, of the QRS complex may increase as the height or amplitude of the waveform increases due to changes in patient respiration, drift in the signal baseline and/or other causes.

Accordingly, it is a principal object of the present invention to provide a method and apparatus for analyzing the ECG wave in a manner which simply and accurately identifies VPB's. It is a further object of the invention to provide improved means for accurately identifying the occurrence of the QRS complex in an ECG waveform whereby accurate identification of VPB's and other heart characteristics may be made.

REFERENCE TO PRIOR ART

In addition to the aforementioned U.S. patents, the prior art also includes U.S. Pat. No. 3,838,768 issued Aug. 13, 1974. This patent predicates identification of VPB's upon the identification of low frequencies (i.e., 2-10 Hz) in the QRS complex.

Further prior art related to the aforementioned Harris patents includes U.S. Pat. No. 3,807,392 issued Oct. 26, 1971, comprising a computer-based counterpart of U.S. Pat. No. 3,616,791, and U.S. Pat. No. 3,616,790 issued Nov. 2, 1971.

SUMMARY OF THE INVENTION

The present invention is based on the recognition that ventricular premature beats may be identified in an ECG waveform in a novel manner which is both simple and accurate. That identification of VPB's is based solely upon the width of a particular QRS complex exceeding an average width for such complexes by a predetermined amount, that width being determined in a novel manner. More specifically, the determination of width for each QRS complex is done indirectly with a measurement of QRS complexes, which area is normalized to remove variations in waveform amplitude by dividing the area by the height thereof. Although this indirect width measure does not result in a signal which is identical to the width of the complex, it does result in a signal which is proportional to that width.

According to a preferred embodiment of the invention, a particular heartbeat is designated a premature ventricular contraction if the QRS complex is determined, using the technique of the invention, to be at least 40% wider than the average width of the immediately-preceding several QRS complexes. Supplementally, a VPB may also be indicated if the width of a QRS complex determined in the manner of the invention is early, exceeds the average width by at least 20% and is additionally followed by a compensatory pause as determined by interbeat interval measurements.

Briefly, in a preferred embodiment, the ECG signal is fed into two parallel filters, the outputs of which are rectified and peak detected. The bandwidth of one filter is characteristically that of a normal QRS complex such that its output is proportional to height. The bandwidth of the other filter is somewhat below that of the former such that the QRS complex evokes the filter's impulse response which is in turn proportional to the area of the complex. The peak-detected area is then divided by the peak-detected height to obtain a width measure which is compared with an average of preceding width measures.

According to another aspect of the invention, an improved R-wave detector is provided, which detector exhibits increased accuracy for controlling the peak detection of the height and area measures of a QRS complex. More particularly, a variable threshold is associated with generally conventional R-wave detection means whereby to increase sensitivity to relatively small amplitude R-waves and decrease sensitivity to T-waves of relatively large amplitude. Both the VPB and the R-wave detection circuitry adapt to individual patients and to variations over time in the QRS complex of a single patient through use of averaging techniques.

DESCRIPTION OF A PREFERRED EMBODIMENT

Figure 1:
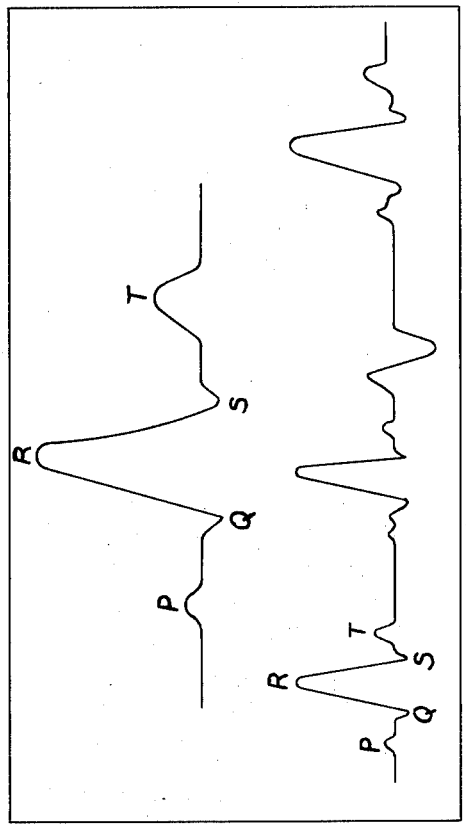
FIG. 1 depicts a typical ECG of an individual having a mixture of normal and abnormal heartbeats, the uppermost trace being the ECG waveform for a single normal heartbeat.

In FIG. 1 there is illustrated in the bottom trace an electrocardiogram (ECG) of a heart patient characterized by a mixture of normal and abnormal beats. The ECG in the upper trace of FIG. 1 represents an enlarged single normal heartbeat of the patient. The different characteristic portions of the waveform are identified by the conventional signals P, Q, R, S and T. In the lower trace, two normal beats spaced at a proper time interval and followed by one abnormal beat which is premature and which is followed by another normal beat. It will be noted that the premature beat follows the second normal beat too closely and is spaced from the final normal beat by more than the normal interval. That increased interval is commonly referred to as the compensatory pause.

Figure 2:
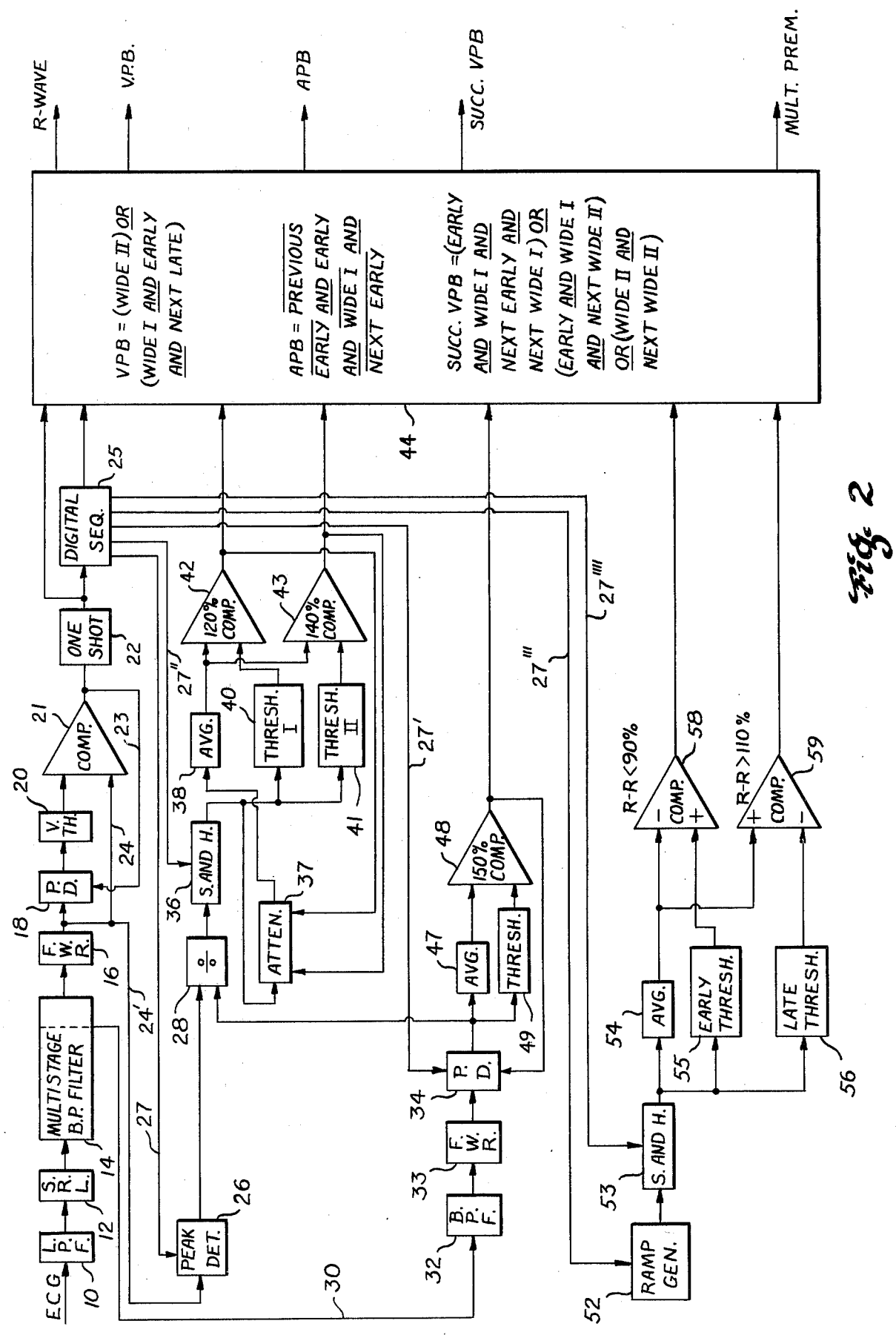
FIG. 2 is a detailed schematic block diagram of apparatus for practicing the invention.

The ECG monitoring systems illustrated in schematic block diagram form in FIG. 2 receives the ECG signal of FIG. 1 as its principal input and analyzes that waveform to detect and indicate the existence of VPB's as well as other types of ectopic beats. In the illustrated embodiment, the circuitry of FIG. 2 is particularly suited for analyzing ECG signals previously recorded, as during ambulatory or Holter-type heart monitoring; however, it will be appreciated that the system is similarly applicable to on-line or real-time situations, as for instance associated with a patient in the intensive care unit of a hospital. The playback of previously recorded ECG signals may occur at the same rate at which the signals were recorded (1×) or, as is often the case, it may occur at 60 or even 120 times (60× or 120×) the speed at which they were recorded. This latter speed-up of playback expedites the analysis of the recorded signal. In the main, the following discussion of the circuitry of FIG. 2 will, for simplicity, assume playback at the same speed (1×) at which recorded. It will, of course, be appreciated that the various time constants associated with the circuitry of FIG. 2 will have one value for a 1× playback speed, a value which is 60 times smaller for a 60× playback speed, and a value 120 times smaller for a 120× playback speed. The capability of selectively processing the ECG signal at multiple playback speeds may be accomplished either by several selective channels each having different appropriate time constants or by a single channel having components with different time constants selectively insertable therein to and removable therefrom. This selectively is relatively easily accomplished in a program-controlled, microprocessor-based system.

Referring to the ECG monitoring or analyzing system of FIG. 2 in greater detail, the ECG signal, derived from the playback heads of a recorder or the like, is connected as an input to low-pass filter 10. Low-pass filter 10, in addition to comprising the input to the overall analyzer system of FIG. 2, is also the first stage of an R-wave detector which additionally includes slew-rate limiter 12, band-pass filter 14, full-wave rectifier 16, peak detector 18, variable threshold 20, comparator 21, and non-retriggerable one-shot 22 to be described in greater detail. Low-pass filter 10 is designed to remove 60 Hz noise (at 1×) from the input ECG signal.

The output of low-pass filter 10 is connected to the input of slew-rate limiter 12 of conventional design and scaled to substantially suppress pacemaker spikes, the noise associated with tape dropout, certain types of muscle artifact and the like. By and large, the signals passed by slew-rate limiter 12 will include normal ECG waveforms, VPB's and other ectopic beats and possible some muscle artifact.

Figure 3:
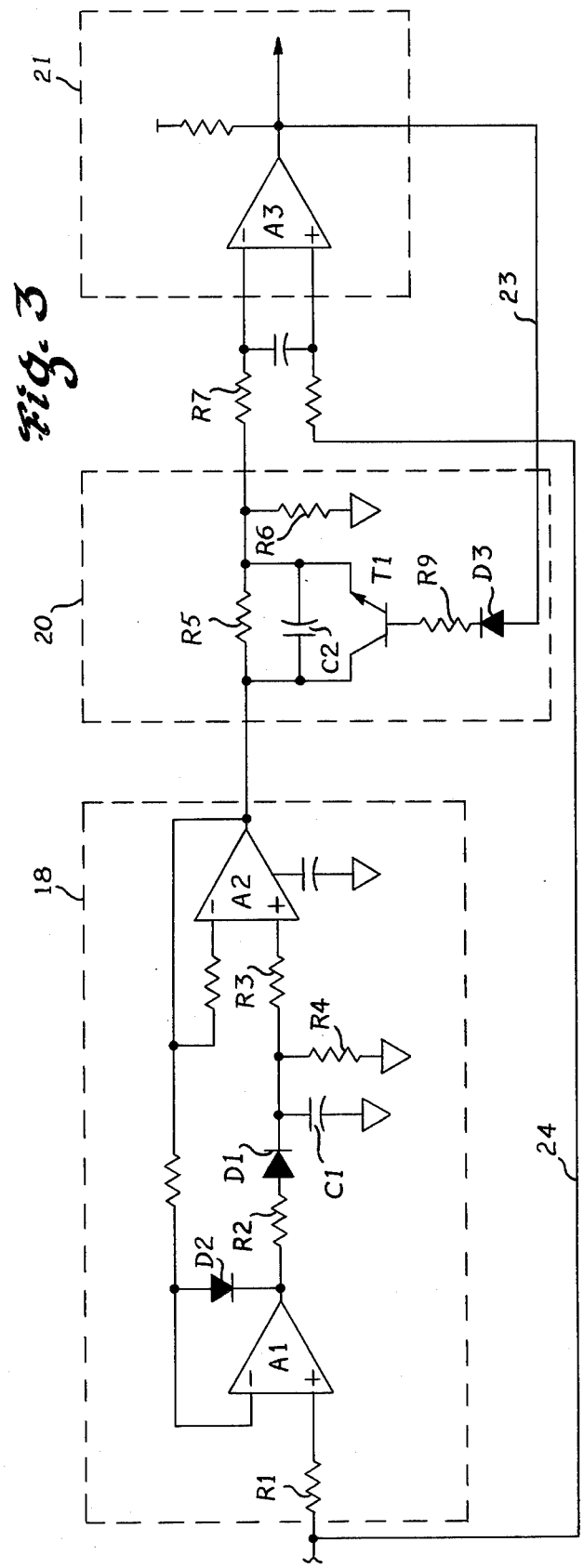
FIG. 3 is a more detailed schematic diagram of certain portions of the R-wave detector forming part of the apparatus of FIG. 2.

The output of slew-rate limiter 12 is applied as the input to multistage band-pass filter 14. A first portion of filter 14, shown in greater detail as part of FIG. 3, is shared by the R-wave detection circuitry as well as the "area" detector to be hereinafter described. The latter portion of filter 14 is utilized only by the R-wave detection circuitry and the waveform height or amplitude detector. The initial or common portion of band-pass filter 14 typically has a band-pass range of 0.8–8 Hz and the final section comprises a high-pass section which, in combination with the preliminary stages, provides an overall band-pass range to the filter of 8–32 Hz for 1× operation. This range of 8–32 Hz is intended to pass not only normal QRS complexes but also those of an ectopic nature. The somewhat lower frequency T-wave component is attenuated to some extent by filter 14.

The output signal from multistage band-pass filter 14 is applied as the input to a full-wave rectifier 16 of conventional design. Rectifier 16 ensures that all signal excursions to either side of the base line subsequently appear on only one side of the base line, thereby obviating need for separate positive and negative threshold detection which would otherwise be required as a result of the possibly reversed polarities to the input ECG signal as a result of electrode placement on the patient.

The output of full-wave rectifier 16 is applied as the input to peak detector 18 and additionally as one of the two inputs to comparator 21. Whereas filter 10, rate limiter 12, band-pass filter 14 and full-wave rectifier 16 comprise means for "cleaning up" the ECG signal for R-wave detection, peak detector 18, variable threshold 20 and comparator 21 provide the actual means for detecting the R-wave and one-shot 22 provides an indication of same. The combination of peak detector 18, variable threshold 20 and comparator 21 with feedback of the output of comparator 21 to variable threshold 20 via conductor 23 provides novel means for accurately detecting R-waves, even those of relatively small magnitude as may be associated with ectopic beats, without also responding to T-waves, particularly those of relatively large magnitude.

Additional detail to the combination of peak detector 18, variable threshold 20 and comparator 21 may be obtained through a consideration of the schematic of FIG. 3. The output from rectifier 16 of FIG. 2 is applied to the noninverting input of an operational amplifier A1 via input resistor R1. The output of amplifier A1 is extended to the noninverting input of amplifier A2 through the series circuit of a low value resistor R2, a peak detecting diode D1 and an input resistor R3. A capacitor C1 and resistor R4 are connected in parallel to ground from the cathode of diode D1. The capacitor C1 is charged by the rectified voltage pulses corresponding with the R-wave as well as other portions of the ECG signal. The value of resistor R4 in combination with the value of capacitor C1 are selected such that capacitor C1 discharges at a relatively slow rate, for instance, to two-thirds of its value in about five seconds or five heartbeats. The output of amplifier A2 is fed back to the inverting inputs of amplifiers A1 and A2. A clamping diode D2 is connected between the inverting input and the output amplifier A1.

The voltage appearing across capacitor C1 and subsequently at the output of amplifier A2, and thus also the output of peak detector 18 of FIG. 2, reflects the maximum peak voltage, or at least an average of the peak voltages associated with the QRS complexes, at the input over the preceding interval of several seconds (1× operation). Typically the R-wave is responsible for the largest peak voltage in the ECG waveform during each heartbeat, such that whether it is the largest peak over several heartbeats or a value more nearly to an average of the peaks over that interval appearing at the output, that output value is representative of the peak value of one or more QRS complexes during that interval. This value is applied to the input of variable threshold circuit 20 for variable scaling and subsequent application as the reference input to comparator 21. Although described as a peak detector, it will be appreciated that circuit 18 may embody the teachings of the aforementioned U.S. Pat. No. 3,490,811 such that the output is clearly an average of the peaks.

Variable threshold 20 includes a voltage divider comprised of resistors R5 and R6 with one end of R5 being connected to the output of peak detector 18 and one end of R6 being connected to ground, the junction between R5 and R6 being connected through input resistor R7 to the inverting or reference input of amplifier A3 of comparator 21. The values of resistors R5 and R6 are scaled such that, at steady state, the threshold value applied to comparator 21 is normally about 40% of the peak value provided as the output from peak detector 18. The signal output from rectifier 16 is also led directly to the other input of comparator 21 via lead 24. The signal amplitude on lead 24 is compared by amplifier A3 with that provided by variable threshold 20. The normally relatively low voltage at the output of amplifier A3 goes relatively more positive whenever the rectified ECG signal exceeds the instantaneous threshold value. This positive transition in the voltage at the output of amplifier A3 is developed across resistor R8 and serves as the trigger input to non-retriggerable one-shot 22. When one-shot 22 is triggered, it provides a positive pulse of approximately 180 milliseconds duration for signifying the occurrence of an R-wave and keying the operation of a digital sequencer 25.

In addition to triggering one-shot 22, the positive going voltage at the output of comparator 21 is fed back via lead 23 through diode D3 and base resistor R9 to the base of transistor T1. A capacitor C2 is connected to parallel across resistor R5 and the emitter and collector of transistor T1 are similarly connected in parallel across resistor R5 and capacitor C2. Immediately prior to the occurrence of the R-wave in a particular ECG waveform, capacitor C2 will be substantially fully charged and the threshold voltage appearing at the junction of resistors R5 and R6 will be about 40% that of the output of peak detector 18. However, as soon as the amplitude of the present R-wave exceeds the threshold value and evokes a positive response from comparator 21, the positive going voltage on lead 23 operates to turn on transistor T1, thereby relatively short-circuiting capacitor C2 and resistor R5 and applying substantially the full (i.e., 100%) value appearing at the output of peak detector 18 as the threshold value to the reference input of comparator 21. This has the effect of greatly increasing the threshold for any relatively large T-waves which may follow as QRS complex. Stated another way, the variable threshold enables increased sensitivity to small amplitude R-waves without requiring the threshold to remain so low as to additionally detect the following T-waves. As the threshold reference value rapidly increases to near 100% of the output of peak detector 18, it will soon no longer be exceeded by the input appearing on line 24. Accordingly, the output of comparator 21 drops to its normal potential, thereby returning transistor T1 to nonconduction. The RC time constant of capacitor C2 and resistor R5 in parallel with resistor R6 is such that recharge of capacitor C2, and thus return of the threshold network to its normal 40% value, occurs continuously over an interval sufficiently long to exclude T-waves but sufficiently short to anticipate the next succeeding R-wave. A typical RC time constant is about 200–300 milliseconds and 1× operation. Although more difficult, it will be understood that the variable scaling might instead be applied to the rectified ECG signal from rectifier 16, except that the function would be inverted, i.e., the ECG signal would be amplified by 2½ times until R-wave detection whereupon it would return to normal amplitude to "miss" the T-wave then gradually increase to 2½ times to detect the next R-wave.

Returning to the discussion of FIG. 2, attention is given another portion of the ECG monitoring system comprising a principal aspect of the invention. The output of full-wave rectifier 16 is additionally extended via line 24' to the input of peak detector 26. Peak detector 26, in addition to conventional peak detecting circuitry of a type hereinbefore described, also includes hold circuitry for presenting to the output thereof only the peak rectified signal commensurate with a QRS complex. A gating or reset signal is provided via line 27 from digital sequencer 25 to the reset input associated with the hold portion of peak detector 26. Digital sequencer 25 is of conventional design and is driven by a clock, not shown. The R-wave indication provided by one-shot 22 serves to initiate certain predetermined sequences of control signals provided by sequencer 25. Accordingly, the reset signal appears on line 27 for only a brief interval immediately after an R-wave has been detected to reset the hold circuit for permitting detector and hold circuit 26 to respond to the present QRS complex. The output of peak detector 26 is proportional to the "height" of the QRS complex and is extended to the denominator input of a divider 28.

Figure 4:
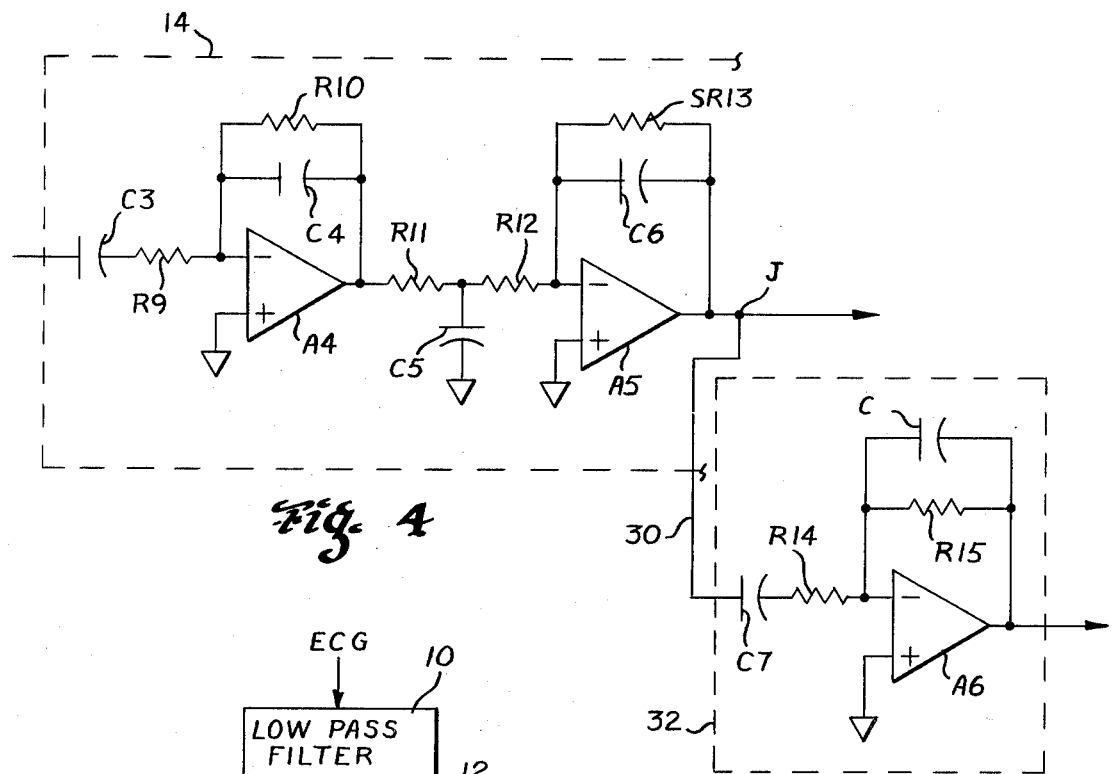
FIG. 4 is a more detailed schematic diagram of a band-pass filter utilized for its impulse response in the apparatus of FIG. 2.

To obtain a measure of the area of the QRS complex of the input ECG waveform, the signal is led from an intermediate section of the multistage band-pass filter 14 via lead 30 to an additional band-pass filter 32. The characteristics of the preliminary stage of filter 14 and the band-pass filter 32 are selected such that the impulse response thereof to the QRS complex will provide an accurate measure of the area of the QRS complex. Referring to the preliminary stages of multistage band-pass filter 14 in FIG. 4, the ECG signal passes through a first filter stage including amplifier A4 and a second filter stage including amplifier A5 to junction J, then lead 30 to filter 32. The input to amplifier A4 is through a series-combination of capacitor C3 and resistor R9. A parallel combination of capacitor C4 and resistor R10 is connected between the output and the input of amplifier A4. A "T" network comprised of series resistors R11 and R12, and capacitor C5 therebetween to ground, is connected between the output of amplifier A4 and the input of amplifier A5. A parallel combination of capacitor C6 and resistors R13 is connected between the output and input of amplifier A5. The values of capacitors C3–C6 and resistors R9–R13 are selected to provide a band-pass range of about 0.8–8 Hz at 1× operation, or may be selected to provide a 40 Hz–470 Hz passband for 60× operation, etc.

Band pass filter 32 includes amplifier A6, the series combination of capacitor C7 and resistor R14 in lead 30 to the input thereof, and the parallel combination of resistor R15 and capacitor C8 extending between the output and input thereof. The values of these resistances and capacitances are selected such that the filter individually has a passband range of about 2–20 Hz during 1× operation, but when considered in conjunction with the earlier stages of filtering a filter 14, the band-pass between the input to filter 14 and the output of filter 32 is in the range of about 2–8 Hz for 1× operation. It will be appreciated that the upper end of this passband then is lower than most of the instantaneous frequency characteristics of portions of the QRS complex. For this reason, the output from filter 32 does not accurately follow the QRS complex but instead provides a ringing impulse response therefor. The amplitude or magnitude of the impulse response is proportional to the energy content, and thus the area, of the QRS complex. By noting the magnitude of this impulse response, it is then possible to use that value as the measure of area of the QRS complex, which value is supplied to the numerator input of divider 28.

Accordingly, the output of band-pass filter 32 is extended to the input of a full-wave rectifier 33 which is similar in structure and function to that of full-wave rectifier 16. The output of full-wave rectifier 33, which will comprise pulses of a single polarity, are extended to the input of peak detector 34 which is similar in structure and function to peak detector 26. Peak detector 34 detects the peak values of the rectified impulses resulting from the outout of band-pass filter 32, and a sample-and-hold circuit associated therewith records those peak values. The sample-and-hold associated with peak detector 34 receives a gating or sampling pulse via line 27' from sequencer 25 which extends approximately 180 milliseconds from detection of an R-wave. Both the "height" peak detector 26 and the "area" peak detector 34 note the respective peak amplitudes of the input signals during the predetermined 180 millisecond interval mentioned above during which the respective signals have experienced peak magnitude.

Divider 28 is of conventional design and serves to divide the numerator signal value of the QRS "area" from peak detector 34 by the denominator signal value of the QRS "height" value from peak detector 26. The resulting output from divider 28 is a normalized measure of the area, which is proportional to the width, of the QRS complex, which indirect measure of width is then utilized to determine the existence of a VPB.

By dividing the area of the QRS complex by its height, variations to the area as a result of changes in the amplitude of the ECG waveform are normalized. In other words, the output of divider 28 provides an indirect measure of the width of a QRS complex without relying solely on the measure of the area for that result. The output of divider 28 is connected to the input of a sample-and-hold circuit 36 which, in response to a sampling pulse applied thereto on line 27" from sequencer 25, records and holds the indirect measure of width. The sampling signal on line 27" occurs almost immediately after the sampling pulse associated with peak detectors 26 and 34.

The output of sample-and-hold 36 is extended to the inputs of a first or lower level threshold circuit 40 and a second or higher level threshold circuit 41 and also, by way of selectively controllable attenuator 37, to the input of averager 38. Attenuator 37 is of conventional voltage divider-type design and normally introduces no attenuation to the "width" signal supplied to the input of averager 38. Averager 38 is of conventional design and averages the indication of "width" for several successive heartbeats, i.e., about five seconds under 1X operation. The averaged value of several successive "width" measures is extended from the output of averager 38 to the respective reference inputs of comparators 42 and 43. The current or instant values of "width" are applied to threshold circuits 40 and 41, the respective outputs of which comprise the variable inputs to comparators 42 and 43 respectively. Threshold circuits 40 and 41 each comprise conventional voltage divider circuits with the respective voltage dividers being scaled such that the output from circuit 40 is about five-sixths or 83% of the input thereto and the output of circuit 41 is about five-sevenths or 71% of the input thereto. Stated another way, the instant "width" signal seen at comparator 42 will exceed that applied by averager 38 only when it exceeds 120% of the average "width" signal before passing through threshold circuit 40 and the instant width signal seen at the input of comparator 43 will exceed that applied by averager 38 only when it exceeds 140% of the average value before passing through threshold circuit 41. Accordingly, the output of comparator 42 shifts to a relatively more positive potential whenever and so long as the instant width value exceeds the average width by 120% or more, and the output of comparator 43 shifts to its positive level whenever and so long as the instant width exceeds 140% of the average value. These relatively positive output levels of comparators 42 and 43 are respectively designated WIDE I and WIDE II. As with the signal from one-shot 22 indicating the occurrence of an R-wave, the WIDE I and WIDE II signals are applied to logic unit 44 where they are utilized for determining the occurrence of VPB's, atrial premature beats (APB's), successive VPB's and the like, as will be described.

Because it may be generally undesirable to substantially distort the average "width" value provided by averager 38 when an abnormally wide QRS complex occurs, attenuator 37 is automatically operative to dilute or attenuate the effect of such "wide" value on the average provided by circuit 38. More specficially, the WIDE I and WIDE II outputs are extended via lines 45 and 46 respectively to respective control inputs of attenuator 37. The WIDE I signal is operative to introduce a 10% attenuation factor to the instant width signal subsequently extended to the input of averager 38. The WIDE II signal is also operative to introduce an additional amount of attenuation, for instance, 10–20%, to the instantaneous value supplied to the input of averager 38. In this way, the average value of several successive "width" measures is not seriously distorted by occasional wider QRS complexes.

Returning to "area" peak detector 34, its output is additionally extended to the input of averager 47 which is identical to averager 38. The output of averager 47 is extended to the reference input of comparator 48. The output of "area" peak detector 34 is also extended through threshold circuit 49 to the other or variable input of comparator 48. Threshold circuit 49 comprises a voltage divider scaled to provide an output which is two-thirds or 66% of its input. In other words, the input to comparator 48 provided by the instantaneous "area" signal will equal the average "area" value provided by averager 47 when the former, prior to passage through threshold circuit 49, is 150% of the latter. Therefore, the output of comparator 48 will shift to its positive level whenever and so long as the instantaneous "area" value is 150% or more of the average "area" value. This output value from comparator 48 is designated LARGE AREA and is extended as an optional input to logic system 44 and may be used to detect VPB's in the classical manner.

Additionally, the LARGE AREA output of comparator 48 is fed back via line 50 to a control input of peak detector 34 in substantially the same manner and for substantially the same purpose as the WIDE I and WIDE II controls for attenuator 37. Specifically, an attenuating or bleed resistor (not shown) associated with peak detector-sample-and-hold circuit 34 is connected into that circuit by an electonic switch (not shown) by the occurrence of a LARGE AREA signal on line 50 to attenuate the signal which subsequently appears at the output of detector 34. This action occurs only after the instant actual "area" value has been presented to divider 28 and the "width" measure stored in sample-and-hold 36. By thereafter attenuating the output of peak detector 34, the "area" input to averager 47 will deviate less from the average than previously. Also, as the output of peak detector 34 declines, so too will its input to comparator 48 via threshold circuit 49 until the apparent "area" value is no longer greater than 150% of the average, whereupon the attenuation control via line 50 is interrupted. The instantaneous "area" value will continue then at the 150% of average level until the next QRS complex.

Circuitry is provided for monitoring the interval between successive QRS complexes for indicating if a QRS complex occurs earlier or later than some average-interval range established by the interval between several preceding QRS complexes. A ramp generator 52 initiates a voltage ramp of predetermined slope or ramp rate in response to a reset and trigger signal provided by digital sequencer via line 27'''. The reset and trigger to ramp generator 52 occurs a predetermined fixed interval after the recognition of an R-wave, i.e., 180 milliseconds. The output of ramp generator 52 is connected to the input of sample-and-hold circuit 53. A sampling signal is extended to sample-and-hold 53 from digital sequencer 25 via line 27'''' and is timed to store that output of ramp generator 52 existing a brief interval prior to reset of ramp generator 52. In this way the value stored in sample-and-hold 53 is substantially proportional to the interval between successive R-waves, being only slightly less than the actual value. The output of sample-and-hold 53 is extended to the respective inputs of threshold circuits 55 and 56 to the input of averager 54.

Averager 54 is substantially identical to averagers 36 and 47. The averager of the several (i.e., five) immediately-preceding R—R intervals appearing at the output of averager 54 is applied to the respective reference inputs of comparators 58 and 59 respectively. Both threshold circuits 55 and 56 are scaled to provide outputs which are about nine-tenths or 90% of their respective inputs; however, the output of threshold 55 is connected to the noninverting input of comparator 58 whereas the output of threshold 56 is connected to the inverting input of comparator 59. In this way, the output of comparator 58 moves to a relatively positive voltage level to provide an EARLY signal whenever the instantaneous R—R interval is less than about 90% of the average R—R interval, and the output of comparator 59 moves to a relatively positive voltage level to provide a LATE signal whenever the instantaneous R—R interval is greater than about 110% of the average R—R interval. The outputs of comparators 58 and 59 providing the respective EARLY and LATE signals are extended to logic system 44.

It may be desirable that a very early complex or a succession of early complexes should not be allowed to distort the average. Means may be employed to detect these conditions and selectively change the time constant of averager 54.

Referring to logic 44, a detailed analysis thereof is not undertaken in the interest of brevity and because a statement of the relavant logic expressions is believed sufficient to enable one of ordinary skill in the art to practice that aspect of the invention. The R-wave pulse provided by one-shot 22, in addition to being a key input to digital sequencer 25 for initiating each cycle of the sequencer, is also extended to and through logic 44 to comprise an output therefrom for utilization by any ancillary circuitry. Logic 44 is structured to provide an output indication of the occurrence of a VPB under either of the following two logic conditions, (1) a WIDE II indication by comparator 43 or (2) the indication of WIDE I by comparator 42 and an EARLY indication by comparator 58 and a subsequent indication by comparator 59 that the next QRS complex is late. In providing the logic for the EARLY and next LATE determinations, it will, of course, be necessary to provide one stage of delay or storage, as by the use of a flip-flop as is well known in the art. It should be understood that the 120% and 140% threshold values suggested for establishing WIDE I and WIDE II respectively in the illustrated embodiment, while being generally preferred, are certainly not limiting and some range of variation is within the scope of the invention.

Logic 44 indicates an atrial premature beat (APB) with logic that recognizes the occurrence of the following conditions: an EARLY QRS complex which is also not WIDE I and neither the previous nor the following QRS complexes are EARLY.

Logic 44 also provides an indication of successive VPB's when one of the following logic conditions is satisified: (1) a QRS complex is EARLY and WIDE I and the next QRS complex is EARLY and is also WIDE I, (2) a QRS complex is EARLY and WIDE I and the next complex is WIDE II, or (3) a QRS complex is WIDE II and the next complex is WIDE II.

Figure 5:
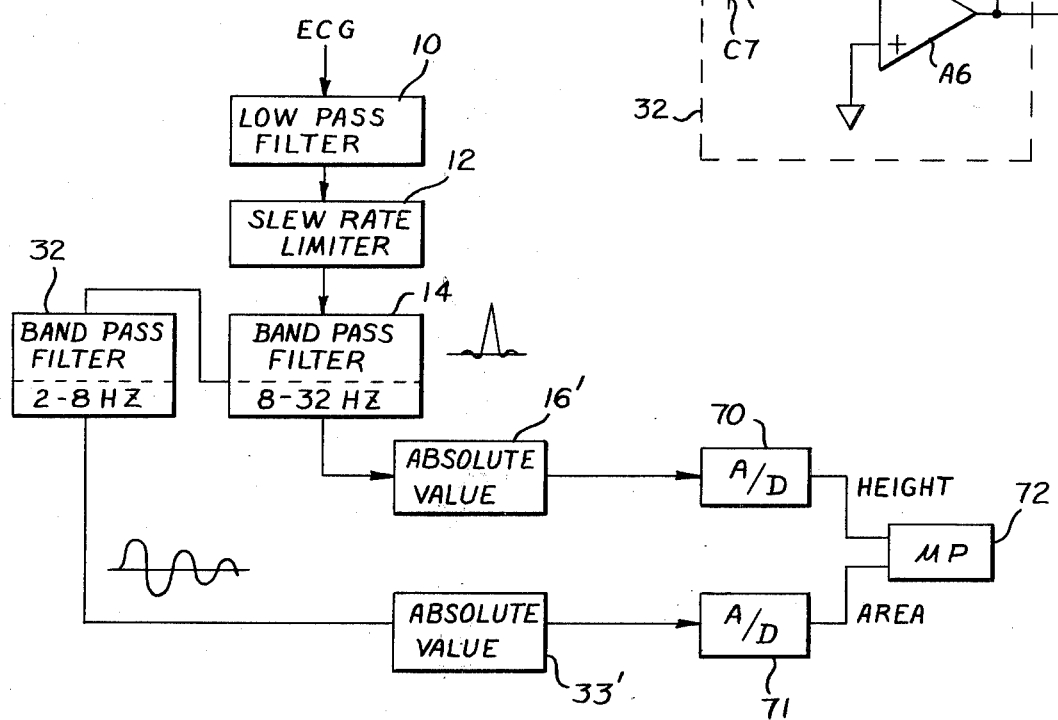
FIG. 5 is a flow diagram of a combined hard-wired and computer-based hybrid of the circuitry of FIG. 2.

Although the invention has been described in the context of a hard-wired system including mostly analog circuitry with some digital sequencing and logic circuits, it will be recognized by those practiced in the art that implementation of the invention by means of a programmable computer or microprocessor is readily available. While implementation entirely with digital circuitry and a microprocessor may be possible, it is preferable that the input stages involving rate limiting and filtering be accomplished in the analog domain with the following signal processing being provided by a programmable microprocessor as illustrated in FIG. 5. In that figure, low-pass filter 10, slew-rate limiter 12, multistage band-pass filter 14 and band-pass filter 32 are identical to those illustrated in FIG. 2, retaining the same reference numerals. The output of band-pass filter 14 is passed through an absolute value circuit 16' analogous to full-wave rectifier 16. Similarly, the output of band-pass filter 32 is passed through an absolute value circuit 33' analogous to full-wave rectifier 33. The output signals from absolute value circuits 16' and 33' respectively are extended to the inputs of analog-to-digital converters 70 and 71 respectively for conversion from analog to digital form. The output signal from A-to-D converter 70 is designated HEIGHT and represents the digital absolute value representations of the signal passed by filter 14. The output signal from A-to-D converter 71 is designated AREA and is a digital representation of the absolute value of the impulse response of filter 32. It will be appreciated that neither of these signals is yet an actual measure of the height or the area of the QRS complex but will respectively be used to provide same. The digital "height" and "area" signals are respectively connected to the inputs of a suitable microprocessor 72 for subsequent processing.

Figure 6A:
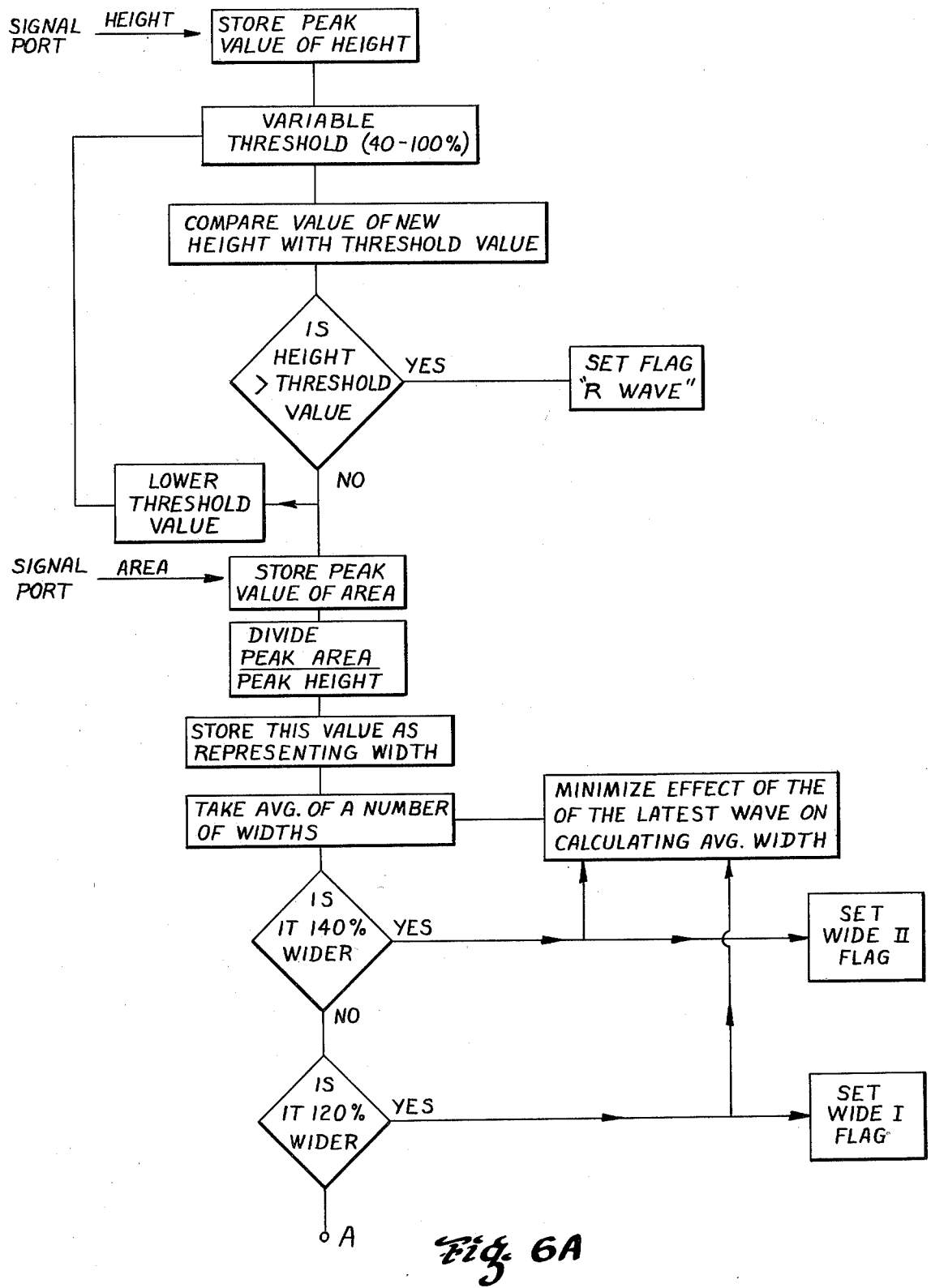
FIG. 6A and 6B in combination comprise the general flow diagram for the programmed computer-based portion of FIG. 5.
Figure 6B:
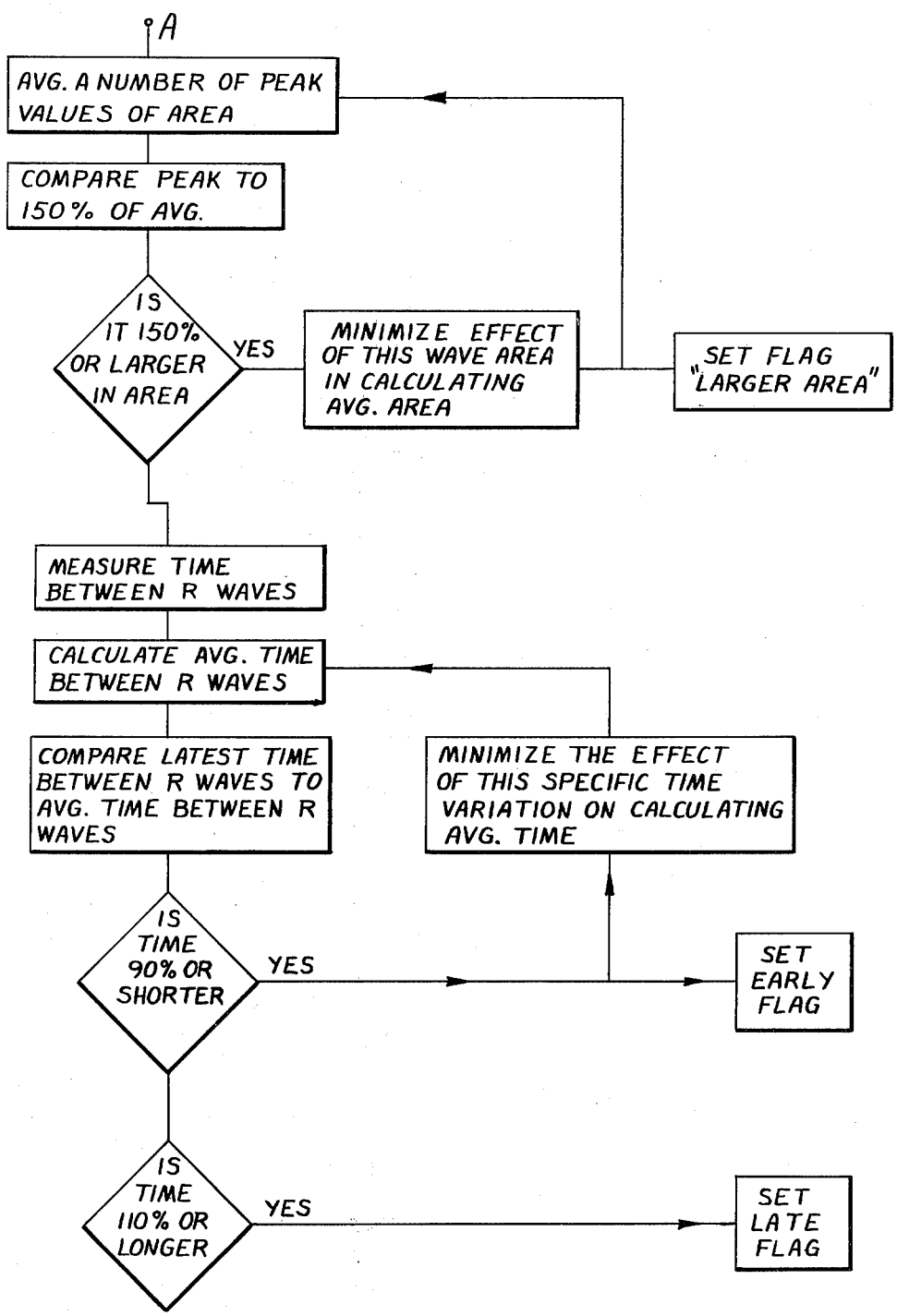

Referring to the flow chart appearing in FIGS. 6A and 6B, to be considered as one, there is illustrated the sequence of control and decision making implementable by program on microprocessor 72. Firstly, the peak value of the successive "height" signals are successively stored. Then, using those stored peak values, a variable threshold is established, which threshold may approach 100% of the stored peak value immediately after detection of an R-wave and declines therefrom to a value of about 40% in the normal interval to the next R-wave. Successive values of new "height" signals associated with the next QRS complex are then compared with the variable threshold value. If the value of a new "height" signal is less than the threshold value, the control loop operates to permit continued reduction of the variable threshold level toward the 40% level. If no R-wave is detected after some time, i.e., two or three normal R—R intervals, then the threshold could be further reduced. If, on the other hand, the new "height" signal exceeds the threshold value, this signifies the occurrence of an R-wave and an "R-WAVE" flag is set.

Upon indication of the occurrence of an R-wave, the peak value of the AREA signal is stored as a measure of area. Subsequently, the stored peak value of area is divided by the stored peak value of height to provide a value which is an indirect measure of the width of the respective QRS complex, which measure is then stored. That value and several (i.e., four) immediately-preceding stored values of width are averaged to provide an average value of width. The stored value representing width is compared with the average value of widths to determine first if it is at least 140% wider than the average width and secondly if it is at least 120% wider than the average width. If at least 140% wider, a "WIDE II" flag is set. If at least 120% wider, a "WIDE I" flag is set. Further, if at least 120% wider than average, the effect of the most recently stored value of width on the average is minimized by a first amount, and if at least 140% wider, the effect on the average is reduced by an even greater amount.

The present stored peak value of area and the previous several stored peak values of area are averaged to provide an average value of area. The most recently stored peak value of area is compared with 150% of the average peak value of area and, if the former is larger than the latter, a "LARGER AREA" flag is set. Also, if the instant value of area is more than 150% of the average value of area, the value of the former in computing the average is minimized. The interval between the setting of successive R-WAVE flags is measured to provide the measure of R—R interval. The interval between the present R-wave and the immediately-preceding R-wave, together with the intervals between the several immediately previous R-waves are averaged to provide an average R—R interval. The most recent R—R interval is compared with the average R—R interval and, if the former is less than 90% of the latter, an "EARLY" flag is set. If the most recent R—R interval is greater than 110% of the average R—R interval, a "LATE" flag is set. If the most recent R—R interval is less than 90% of the average R—R interval, the effect of the former in determining the latter is minimized.

The flow charts of FIGS. 5, 6A and 6B and the foregoing discussion provide ample basis for one of ordinary skill in the programming arts to implement the teachings of the invention in a microprocessor-based system as well as a hard-wired analog system.

The invention may be embodied in other specific forms without departing from the spirit or essential characteristics thereof. The present embodiments are, therefore, to be considered in all respects as illustrative and not restrictive, the scope of the invention being indiciated by the appended claims rather than by the foregoing description, and all changes which come within the meaning and range of equivalency of the claims are therefore intended to be embraced therein.

We claim:

1. An ECG monitoring system comprising means responsive to an ECG waveform for providing a measure proportional to the area of the QRS complex of said ECG waveform, means responsive to the ECG waveform for providing a measure proportional to the peak height of the QRS complex of said ECG waveform, and means for dividing said area measure by said peak height measure thereby to provide a normalized measure proportional to the width of the QRS complex of said ECG waveform.

2. The ECG monitoring system of claim 1 further including means for deriving the average width measure over a plurality of successive ECG waveforms and means for comparing a said width measure with said average width measure derived from previous width measures and in response to said width measure exceeding said average width measure by a predetermined amount for registering a particular wide pulse condition for the respective QRS complex.

3. The ECG monitoring system of claim 2 including means responsive to said particular wide pulse condition for generating a ventricular premature beat signal.

4. The ECG monitoring system of claim 3 wherein said predetermined amount by which said width measure must exceed said average width measure for registering said particular wide pulse is substantially greater than 20%.

5. The ECG monitoring system of claim 4 wherein said predetermined amount by which said width measure must exceed said average width measure for registering said particular wide pulse is about 40%.

6. The ECG monitoring system of claim 3 further including means for comparing a said width measure with said average width measure derived from previous width measures and in response to said width measure exceeding said average width measure by an other amount less than said predetermined amount for registering a different particular wide pulse condition, means for providing a measure of the interval between successive QRS complexes, means for comparing said interval measure with an average of said interval measures over a plurality of immediately preceding QRS complexes and generating an "early" signal of said interval is less than about 90% of said average interval measure or a "late" signal if said interval is greater than about 110% of said average interval measure, and logic means responsive to said different particular wide pulse condition and a commensurate "early" signal and a "late" signal for the next occurring QRS complex for generating a ventricular premature beat signal.

7. The ECG monitoring system of claim 6 wherein said means for determining said average width measure includes averaging means receiving said width measures of successive ECG waveforms for averaging, and attenuating means connected intermediate said dividing means and said averaging means, said attenuating means being responsive to the occurrence of a said particular wide pulse condition for attenuating the amplitude of the respective said width measure by a first predetermined amount and to the occurrence of said different particular wide pulse condition for attenuating the amplitude of the respective said width measure by a second predetermined amount, thereby to reduce its effect on the average.

8. The ECG monitoring system of claim 2 wherein said means for determining said average width measure includes averaging means receiving said width measures of successive EDG waveforms for averaging, and attenuating means connected intermediate said dividing means and said averaging means, said attenuating means being responsive to the occurrence of a said particular wide pulse condition for attenuating the amplitude of the respective said width measure by a predetermined amount, thereby to reduce its effect on the average.

9. The ECG monitoring system of claim 1 including filter means principally responsive to frequencies below those characteristically present in the QRS complex of an ECG waveform, whereby the impulse response of said filter means to the QRS complex is proportional to the energy and thus the area of the respective QRS complex, and means responsive to the peak magnitude of said filter impulse response for the respective QRS complex for providing said area measure.

10. The ECG monitoring system of claim 1 wherein said peak height measure is provided by peak detecting means responsive to the QRS complex of an ECG waveform for storing the maximum amplitude thereof.

11. The ECG monitoring system of claim 1 wherein said means for providing said area measure and said peak height measure include means for detecting occurrence of a said QRS complex, said QRS complex detecting means including means responsive to a continuous ECG waveform having a series of QRS complexes therein for providing a value representative of the peak height of at least one QRS complex in an immediately preceding limited plurality of QRS complexes, variable scaling means for scaling one of the instant said ECG waveform and said peak height representing value to be a controllably variable percentage of the other, means for comprising said scaled one of the instant said ECG waveform and said peak height representing value with the other and indicating occurrence of a QRS complex when the instant ECG waveform-based signal exceeds the peak height representing value based-signal; and means responsive to a said indication of QRS complex for controlling variation of said scaling percentage.

12. In an ECG monitoring system, the method of indirectly providing a measure of the width of a QRS complex appearing in an ECG waveform comprising the steps of:

generating from the ECG waveform a signal proportional to the area of the QRS complex;

generating from the ECG waveform a signal proportional to the peak height of the QRS complex; and dividing said area signal by said peak amplitude signal to provide a normalized signal representative of the width of the QRS complex of said ECG signal.

* * * * *

UNITED STATES PATENT AND TRADEMARK OFFICE
CERTIFICATE OF CORRECTION

PATENT NO. : 4,181,135

DATED : January 1, 1980

INVENTOR(S) : Richard P. Andresen et al.

It is certified that error appears in the above-identified patent and that said Letters Patent are hereby corrected as shown below:

In column 1, line 29, delete "of" and insert --or--;

In column 1, line 60, delete "PVB" and insert --VPB--;

In column 3, line 65, delete "systems" and insert --system--;

In column 4, line 27, delete "selectively" and insert --selectivity--;

In column 6, line 23, delete "to" and insert --in--;

In column 7, line 42, delete "resistors" and insert --resistor--;

In column 7, line 53, delete "the" and insert --this--;

In column 13, line 46, delete "of" and insert --if--; and

In column 14, line 10, delete "EDG" and insert --ECG--.

Signed and Sealed this

Second Day of December 1980

[SEAL]

Attest:

SIDNEY A. DIAMOND

*Attesting Officer*  *Commissioner of Patents and Trademarks*